US006344443B1

(12) United States Patent
Liu et al.

(10) Patent No.: US 6,344,443 B1
(45) Date of Patent: Feb. 5, 2002

(54) PEPTIDE ANTAGONISTS OF TUMOR NECROSIS FACTOR ALPHA

(75) Inventors: Richard Y. Liu, Lutz; Kenneth S. Zuckerman, Tampa, both of FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/349,661

(22) Filed: Jul. 8, 1999

Related U.S. Application Data

(60) Provisional application No. 60/092,080, filed on Jul. 8, 1998.

(51) Int. Cl.[7] ......................... A61K 38/08; A61K 38/10

(52) U.S. Cl. ........................... 514/14; 514/16; 530/327; 530/329; 435/7.8

(58) Field of Search ................................ 530/327, 329; 514/14, 16; 435/7.8

(56) References Cited

U.S. PATENT DOCUMENTS

| | | | |
|---|---|---|---|
| 3,791,932 A | | 2/1974 | Schuurs et al. |
| 3,839,153 A | | 10/1974 | Schuurs et al. |
| 3,850,578 A | | 11/1974 | McConnell |
| 3,850,752 A | | 11/1974 | Schuurs et al. |
| 3,853,987 A | | 12/1974 | Dreyer |
| 3,867,517 A | | 2/1975 | Ling |
| 3,879,262 A | | 4/1975 | Schuurs et al. |
| 3,901,654 A | | 8/1975 | Gross |
| 3,935,074 A | | 1/1976 | Rubenstein et al. |
| 3,984,533 A | | 10/1976 | Uzgiris |
| 3,996,345 A | | 12/1976 | Ullman et al. |
| 4,034,074 A | | 7/1977 | Miles |
| 4,098,876 A | | 7/1978 | Piasio et al. |
| 4,439,196 A | | 3/1984 | Higuchi |
| 4,447,224 A | | 5/1984 | DeCant, Jr. et al. |
| 4,447,233 A | | 5/1984 | Mayfield |
| 4,475,196 A | | 10/1984 | La Zor |
| 4,486,194 A | | 12/1984 | Ferrara |
| 4,487,603 A | | 12/1984 | Harris |
| 4,666,828 A | | 5/1987 | Gusella |
| 4,683,202 A | | 7/1987 | Mullis |
| 4,801,531 A | | 1/1989 | Frossard |
| 4,879,219 A | | 11/1989 | Wands et al. |
| 4,925,678 A | | 5/1990 | Ranney |
| 4,959,217 A | | 9/1990 | Sanders et al. |
| 5,011,771 A | | 4/1991 | Bellet et al. |
| 5,167,616 A | | 12/1992 | Haak et al. |
| 5,169,383 A | | 12/1992 | Gyory et al. |
| 5,192,659 A | | 3/1993 | Simons |
| 5,225,182 A | | 7/1993 | Sharma |
| 5,272,057 A | | 12/1993 | Smulson |
| 5,281,521 A | | 1/1994 | Trojanowski et al. |
| 5,753,628 A | * | 5/1998 | Heavner et al. .............. 514/17 |

FOREIGN PATENT DOCUMENTS

WO 9819162 * 5/1997

OTHER PUBLICATIONS

Dinarello CA, Gelfand JA, Wolf SM: Anticytokine strategies in treatment of systemic inflammatory response syndrome. JAMA 269:1829–1834, 1993.

Grewal HP, Mohey el Din A, Gaber L, et al: Amelioration of physiologic and biochemical changes of acute pancreatitis using an anti–TNF–α polyclonal antibody, Amer J Surg 167:214–19, 1994a.

Oppenheim JJ, Rossia JL, Gearing AJH: Clinical applications of cytokines; Role in pathogenesis diagnosis and therapy (Oxford University Press, New York, NY) pp. 1–27, 1993.

Physicans'Desk Reference: pp/ 1654–1658, 1994.

Huston et al, 1991 "Protein engineering of single–chain Fv analogs and fusion proteins" in Methods in Enzymology (JJ Langone, ed.; Academic Press, New York, NY) 203:46–88.

Johnson and Bird, 1991 Construction of single–chain Fvb derivatives of monoclonal antibodies and their production in *Escherichia coli* Methods in Enzymology (JJ Langone, ed.; Academic Press, New York, NY) 203:88–99.

Mernaugh and Mernaugh, 1995 "An overview of phage–displayed recombinant antibodies" in Molecular Methods In Plant Pathology (RP Singh and US Singh, eds.; CRC Press Inc., Boca Raton, FL) pp. 359–365.

* cited by examiner

*Primary Examiner*—Michael Borin
(74) *Attorney, Agent, or Firm*—Kohn & Associates

(57) ABSTRACT

There is provided a method of inhibiting TNF-α from binding to TNF receptors by administering an effective amount of an inhibitory peptide. Also provided is a method of inhibiting TNF-α functions by administering an effective amount of an inhibitory peptide. There also are provided peptides which have TNF-α inhibitory properties. Also provided is a method of inhibiting TNF-α binding to TNF receptors by administering an effective amount of peptides having the amino acid sequences shown in SEQ ID No. 1,2,3,4, wherein the peptides can be administered either singly or in combination.

2 Claims, 5 Drawing Sheets

PEPTIDE ANTAGONISTS OF TUMOR NECROSIS FACTOR ALPHA

CROSS-REFERENCE TO RELATED APPLICATIONS

This application is a conversion of a U.S. Provisional Application Serial No. 60/092,080, filed Jul. 8, 1998, incorporated herein by reference.

BACKGROUND OF THE INVENTION

1. Technical Field

The present invention relates to compositions that interfere with the function of Tumor Necrosis Factor Alpha (TNF-α) for use as therapeutics and diagnostics.

2. Background Art

Cytokines are peptide/protein immunomodulators that are produced by activated immune cells including thymus-derived T lymphocytes (T-cells), B lymphocytes and monocyte/macrophages. The cytokines include interleukins (IL-1 through IL-18), colony stimulating factors (CSFs) for granulocytes and/or macrophages (CSF-G, CSF-M, CSF-GM), tumor necrosis factors (TNFs α & β), and interferons (IFN α, β & γ). There is a large body of evidence currently available which supports the roles of IL-1 and TNF as major mediators of the systemic response to diseases such as sepsis and as activators of the remaining members of the cytokine cascade (Dinarello et al., 1993).

More specifically, tumor necrosis factor (TNF)-α has a broad range of effects on numerous different cell types throughout the body. It induces proliferation in some cell types, activation in other cell types, and release of other cytokines in some cell types. In many pathologic conditions, including inflammatory diseases such as arthritis, inflammatory bowel diseases, and dermatologic disorders, TNF-α is felt to be a major or the major cytokine responsible for inducing the inflammatory changes. TNF-α also may be involved in the survival and proliferation of some malignant cell types. Therefore, it is of considerable interest and potential clinical significance to identify compounds that interfere with the function of TNF-α. Currently, soluble TNF receptors and antibodies to TNF-α are being used clinically and in clinical studies to attempt to compete for TNF-α binding, so as to prevent binding of TNF-α to cellular TNF receptors, which in turn should prevent activation of the receptors on inflammatory cells and prevent and possibly reverse the inflammatory changes that occur in certain types of patients with arthritis.

It would therefore be beneficial to find alternative means to inhibit TNF-α function, particularly discovery of small peptides that could bind to TNF receptors and interfere with the ability of TNF-α to bind to and activate cellular TNF-α receptors. Such molecules are very useful in research studies in vitro. However, more importantly, these molecules have significant clinical usefulness in treating a broad range of inflammatory conditions, arthritis, and cancers.

SUMMARY OF THE INVENTION

According to the present invention, there is provided a method of inhibiting TNF-α from binding to TNF receptors by administering an effective amount of an inhibitory peptide. Also provided is a method of inhibiting TNF-α functions by administering an effective amount of an inhibitory peptide. There is also provided a peptide which has TNF-α inhibitory properties. Also provided is a method of inhibiting TNF-α binding to TNF receptors by administering an effective amount of a peptide having the amino acid sequence shown in SEQ ID No. 1,2,3,4, wherein the peptides can be administered either singly or in combination.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
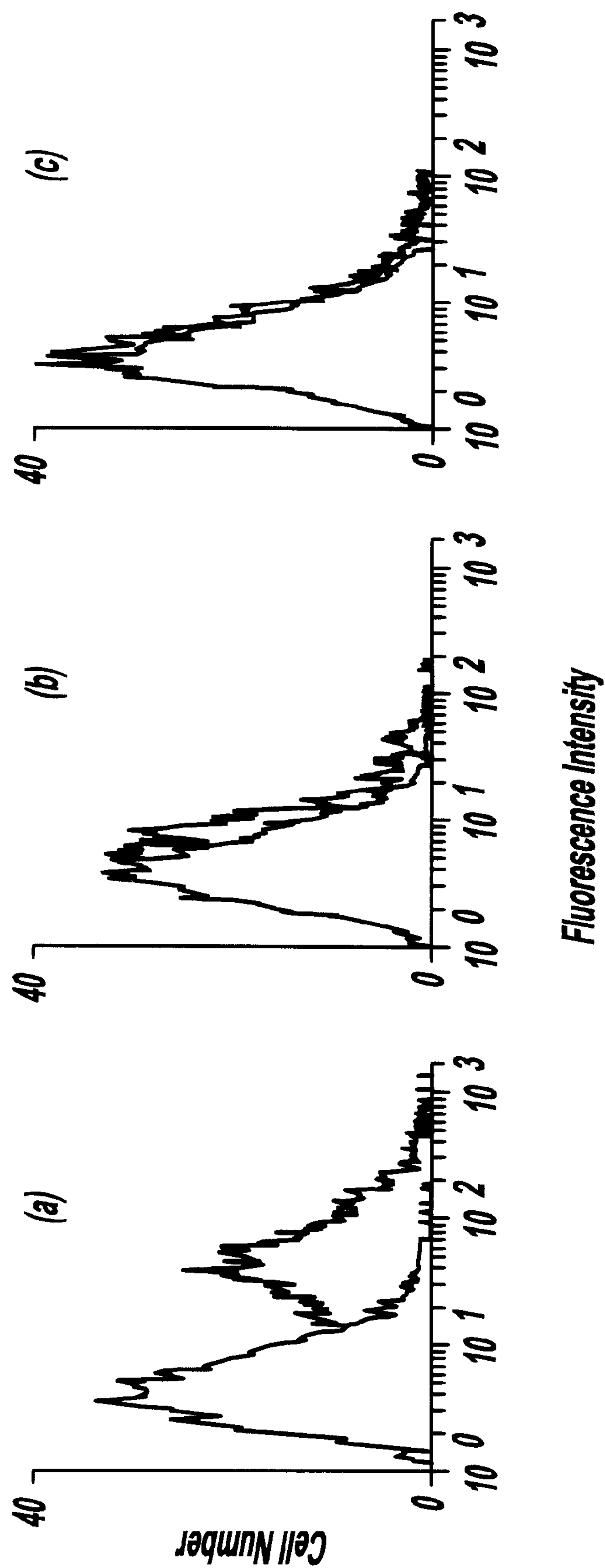
FIGS. 1(*a–c*) is a graph showing the cell number versus the fluorescence intensity of Mo7e cells.

The present invention provides a method for inhibiting TNF-α binding to TNF receptors and TNF-α function by administering an effective amount of an inhibitory peptide. Also provided is a peptide which has TNF-α inhibitory properties.

More specifically, the present invention provides a method of inhibiting TNF-α binding to TNF type I and type II receptors. This is accomplished by administering at least one inhibitory peptide that combines both type I and type II TNF receptors, thus competitively inhibiting the binding of the TNF-α to the receptors, and therefore blocking the functional effects of TNF-α on cells as depicted in FIGS. 1–5.

A phage display library system is used to screen for small peptides that could bind to TNF receptors and prevent the binding of TNF-α to TNF type I receptors and TNF type II receptors. Using this screening system, two 7-amino acid peptides and two 12-amino acid peptides were identified that alone or in combinations bind to both type I and type II TNF receptors, competitively inhibit the binding of TNF-α to the receptors, and blocking the functional effects of TNF-α on cells (i.e., inhibiting the ability of TNF-α to stimulate proliferation of the growth factor-dependent Mo7e leukemic cell line and inhibiting the ability of TNF-α to induce apoptosis of the A549 human lung carcinoma cell line). None of these peptides have identifiable sequence homology to either TNF-α or TNF receptors. The specific TNF-α inhibitory peptides which have been identified and have been synthesized as a result of the phage display library screening and TNF-α inhibitory studies are as follows:

1) Thr-Pro-Lys-His-Leu-Phe-Leu (SEQ. ID NO. 1)

2) Leu-Leu-Gln-Pro-Thr-Met-Asn (SEQ. ID NO. 2)

3) Ser-Val-Ser-Val-Gly-Met-Lys-Pro-Ser-Pro-Arg-Pro (SEQ.ID NO. 3)

4) Phe-Ser-Pro-Leu-His-Thr-Ser-Thr-Tyr-Arg-Pro-Ser (SEQ. ID NO. 4)

The term antagonists or antagonizing is used in its broadest sense. Antagonism, as is used throughout this application, can include any mechanism or treatment which results in inhibition, inactivation, blocking or reduction in TNF-α. For example, the antagonizing step can include blocking cellular receptors for TNF-α.

The compounds (therapeutics) of the present invention as exemplified by small peptides (1) through (4) listed herein above can be administered to patients either singly or in combination. Based on their individual abilities to bind, a combination can be developed to maximize the ability of the peptides to bind at one or both sites.

Additionally, based on the general method disclosed for finding these inhibitory peptides, additional peptides can be found which are functionally equivalent to the peptides disclosed above. More specifically, the method for determining inhibitory peptides includes three steps. First, the phage libraries were screened by ability to bind to TNF receptor types I and II that were bound to culture dishes. Second, the phage libraries were screened by ability to prevent binding of TNF-α binding to the type I and II receptors. And third, the phage libraries were screened by the ability to prevent functional effects of TNF-α on cells that normally have a measurable response to TNF-α.

Phage display libraries were used to identify peptides that could bind to the TNF-α binding site on TNF receptors and either activate the receptors in the absence of TNF-α or block the ability of TNF-α to activate TNF receptors. No agonist peptides were identified by this screening and detection method. However, all of the peptides that are the subject of this application were found to bind to TNF receptors and prevent a range of TNF-α functions. These peptides prevented TNF-α from stimulating the survival and proliferation of human Mo7e leukemic cells and from inducing apoptotic cell death of human A549 lung carcinoma cells.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that it can be administered as the compounds or as a pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intra-arterial, intramuscular, intra-peritoneally, and intranasal administration as well as through intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals and cell cultures exemplified herein which treatment has a length proportional to the length of the disease process and drug effectiveness. The doses may be single doses or multiple doses over a period of several days, or repeatedly over a long period of time for chronic conditions, and are selected depending on the disease being treated. The treatment generally has a length proportional to the length of the disease process and drug effectiveness and the patient species being treated.

When administering the compounds of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, stabilizers to prevent protein and peptide degradation, such as albumin can be added, or others as utilized by companies such as Emisphere Technologies, Inc. and ALZA Technology. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compounds utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compounds of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 μg/kg to 10 mg/kg per day.

The present invention also provides antibodies (monoclonal and polyclonal) directed against the small peptides of the present invention as exemplified in compounds (1)–(4) shown herein above.

The present invention further provides a method of identifying small peptides that bind to TNF or other cytokine receptors and prevent the binding of the cytokine to the cytokine receptor to control their activity by screening a phage display library. This method allows the determination of small peptides that inhibit/interfere with cytokine to cytokine receptors and which do not have sequence homology with either the receptor or cytokine.

These small peptides are being used in clinical studies to inhibit TNF-α binding, so as to prevent binding of TNF-α to cellular TNF receptors, which in turn should prevent activation of the receptors on inflammatory cells and prevent and possibly reverse the inflammatory changes that occur in certain types of patients with arthritis and other inflammatory diseases.

The above discussion provides a factual basis for the use of small peptides as a TNF-α binding inhibitor and as a diagnostic tool. The method used with a utility of the present invention can be shown by the following non-limiting examples and accompanying figures.

EXAMPLES

GENERAL METHODS

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays: In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Antibody Production: Antibody Production: Antibodies may be either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Spring Harbor, N.Y., 1988 and Borrebaeck, *Antibody Engineering—A Practical Guide*, W.H. Freeman and Co., 1992. Antibody fragments may also be prepared from the antibodies and include Fab, $F(ab')_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane Antibodies: A Laboratory Manual, Cold Spring Harbor Laboratory Publications, New York, 1988 and Borrebaeck, *Antibody Engineering—A Practical Guide, W.H. Freeman and Co.,* 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination. *Recombinant Protein Purification*: Marshak et al, "Strategies for Protein Purification and Characterization. A laboratory course manual." CSHL Press, 1996.

EXAMPLE 1

FIG. 1 is a graph showing the binding of synthesized peptide mixture to Mo7e cells. Mo7e cells ($4\times10^5$) were incubated with (a) 100 μM, (b) 10 μM or (c) 0.1 μM of biotin-labeled peptide mixture and were subsequently stained with streptavidin labeled with fluorescein isothiocyanate. The reactions were then analyzed with a FACScan flow cytometer. The shaded areas represent the control without peptide mixture and white areas represent cells treated with peptide mixture. It was therefore determined that the cells treated with the higher concentration of biotin-labeled peptide showed a greater amount of binding.

EXAMPLE 2

Figure 2:
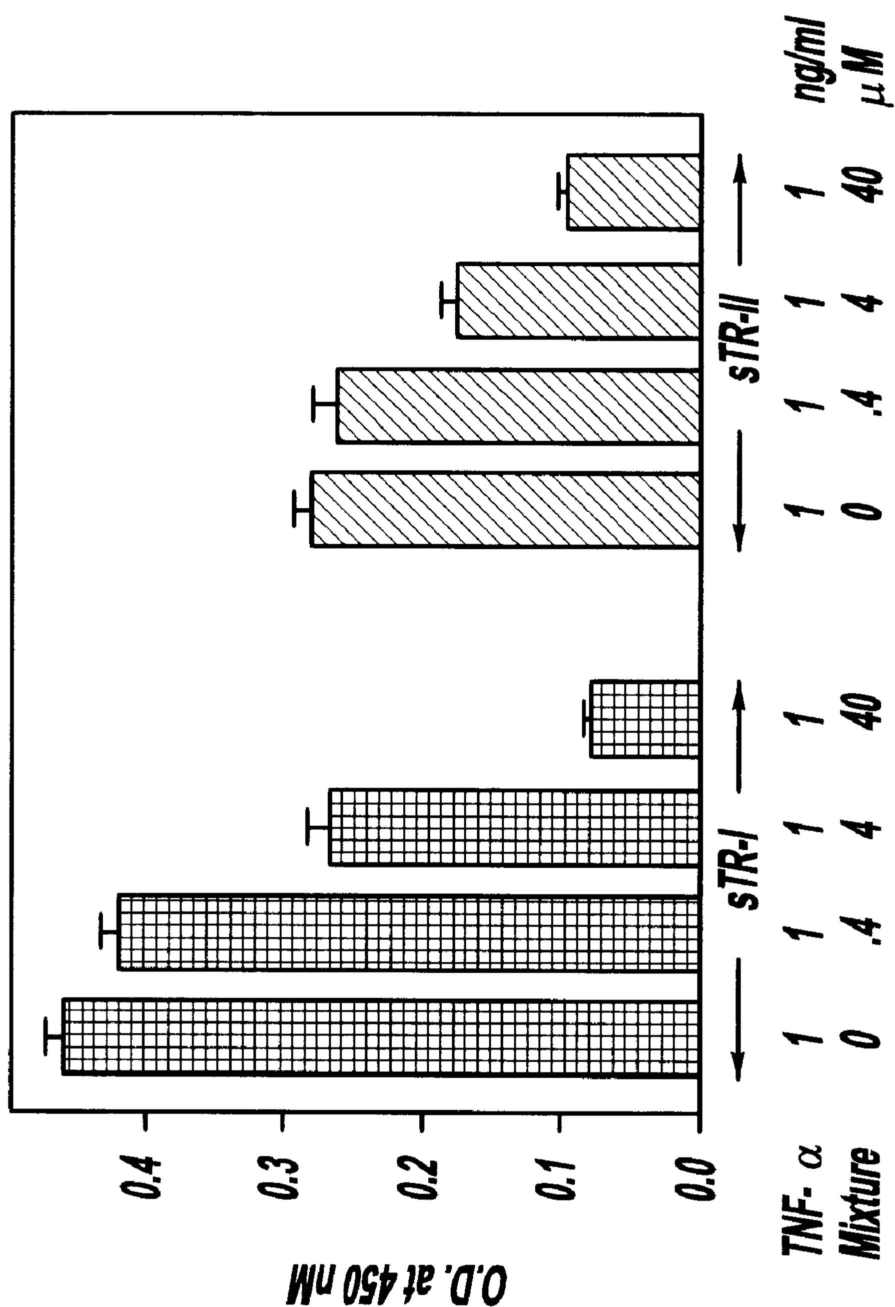
FIG. 2 is a bar graph showing the O.D. at 450 nM versus sTR-I and sTR-II.

FIG. 2 is a graph showing the effect of peptide mixture on the binding of TNF-α to type I or type II TNF receptors. ELISA microplates were pre-coated with 50 ng/ml soluble type I (sTR-1) or type II (sTR-II) TNF receptor. The microplates were then incubated with 1 ng/ml TNF-α and various amounts of peptide mixture. Next, the plates were incubated with anti-TNF-α antibody and subsequently with the second anti-goat IgG antibody labeled with peroxidase. The binding of TNF-α to TNF receptors was revealed by reading at 450 nM. The readings established that the peptide mixture inhibited binding of TNF-α and that this inhibitory property increases with increased concentrations of the peptides.

EXAMPLE 3

Figure 3:
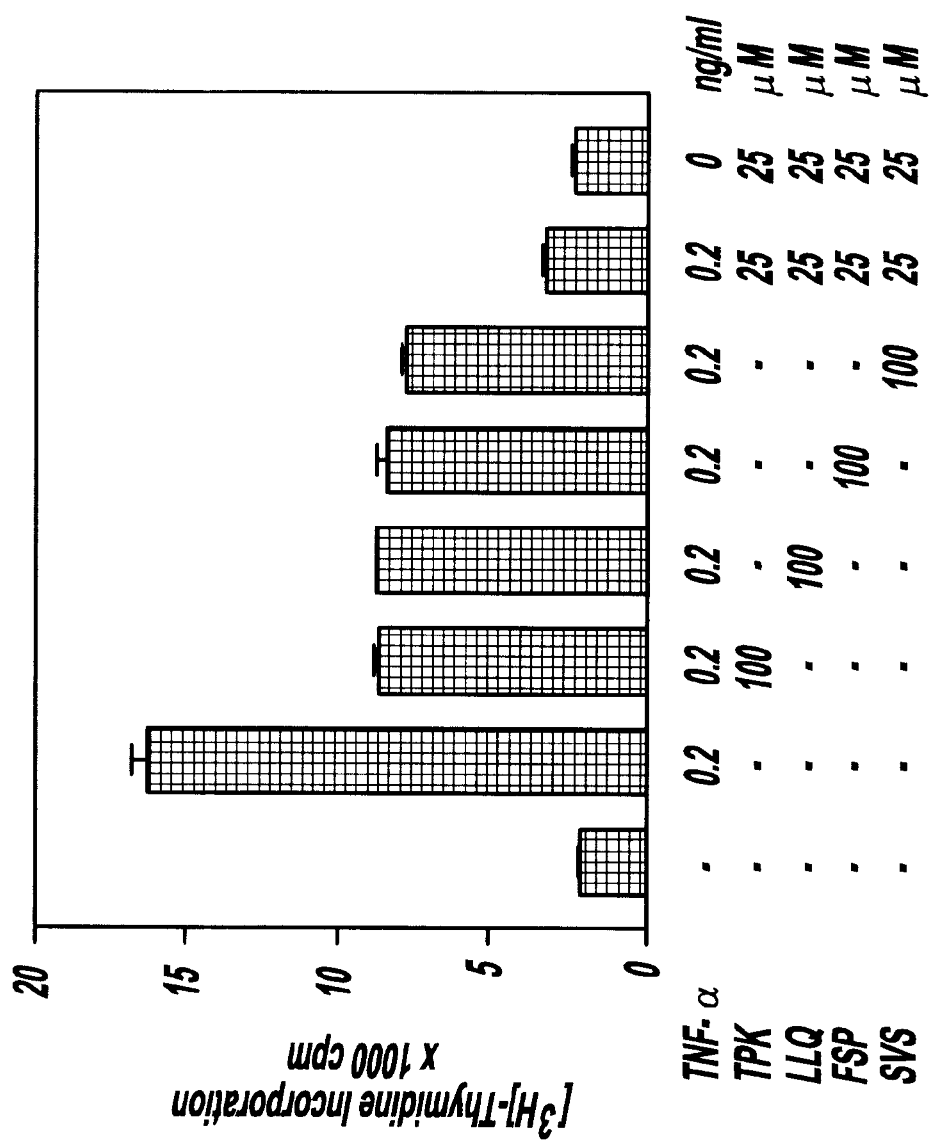
FIG. 3 is a bar graph showing the [$^{3}$H]-thymidine incorporation (×1000 CPM) versus TNF-α (ng/ml), TPK (μM), LLQ (μM), FSP (μM), and SVS (μM)

FIG. 3 is a graph showing the inhibitory effect of peptide mixture on the TNF-α -induced Mo7e cell proliferation. Mo7e cells were pre-incubated in medium without cytokine overnight. The cells were then incubated for three days with no TNF-α (lane 1), 1 ng/ml TNF-α (lane 2), with peptide mixture only (lane 8), with 1 ng/ml TNF-α and 100 μM each of peptides, respectively (lanes 3–6) or with 1 ng/ml TNF-α and peptide mixture (lane 7). Then the cells were labeled with [$^3H$]-thymidine for an additional 4 hours. [$^3H$]-thymidine incorporation was determined from triplicate samples and expressed as mean±SEM of counts per minute of [$^3H$]. The results were similar in three separate experiments performed. The results show that TNF-α function in stimulating proliferation of Mo7e cells is inhibited by each of the peptides alone, and is inhibited to an even greater extent by a combination of the four peptides.

EXAMPLE 4

Figure 4:
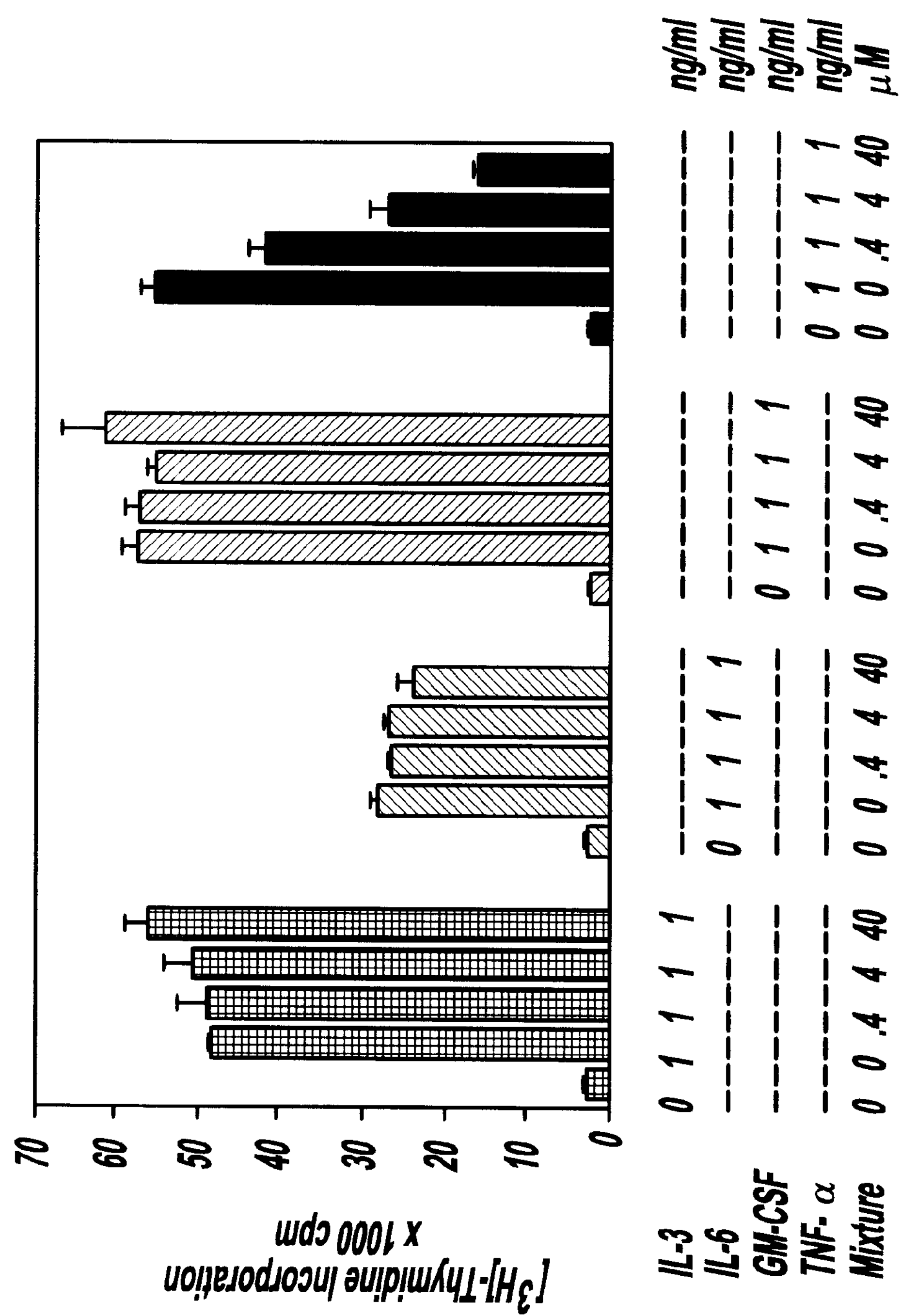
FIG. 4 is a bar graph showing the [$^{3}$H]-thymidine incorporation (×1000 CPM) versus IL-3 (ng/ml), IL-6 (ng/ml), GM-CSF (ng/ml), and TNF-α (ng/ml)

FIG. 4 is a graph showing the effect of each peptide on cytokine-induced Mo7e cell proliferation. Cells were treated for three days without cytokines (lanes 1, 6, 11, 16) with various amounts of peptide mixture and 1 ng/ml IL-3 (lanes 2–5), 1 ng/ml IL-6 (lanes 7–10), 1 ng/ml GM-CSF (lanes 12–15) or 1 ng/ml of TNF-α (lanes 17–20). The cells were then labeled with [$^3H$])-thymidine for an additional 4 hours. [$^3H$]-thymidine incorporation was determined from triplicate samples and expressed as mean±SEM of counts per minute of [$^3H$]. The results were similar in three separate experiments performed. The results showed that TNF-α function is inhibited in a dose-dependent manner, in other words the higher the concentration of the peptide, the greater the inhibition of TNF-α function. Furthermore, the inhibitory effect is shown to be specific for TNF-α. The peptide mixture that potently inhibits TNF-α function has no effect on the ability of several other cytokines, including IL-3, IL-6, and GM-CSF (granulocyte-macrophage colony-stimulating factor) to promote survival and proliferation of human Mo7e leukemic cells.

EXAMPLE 5

Figure 5:
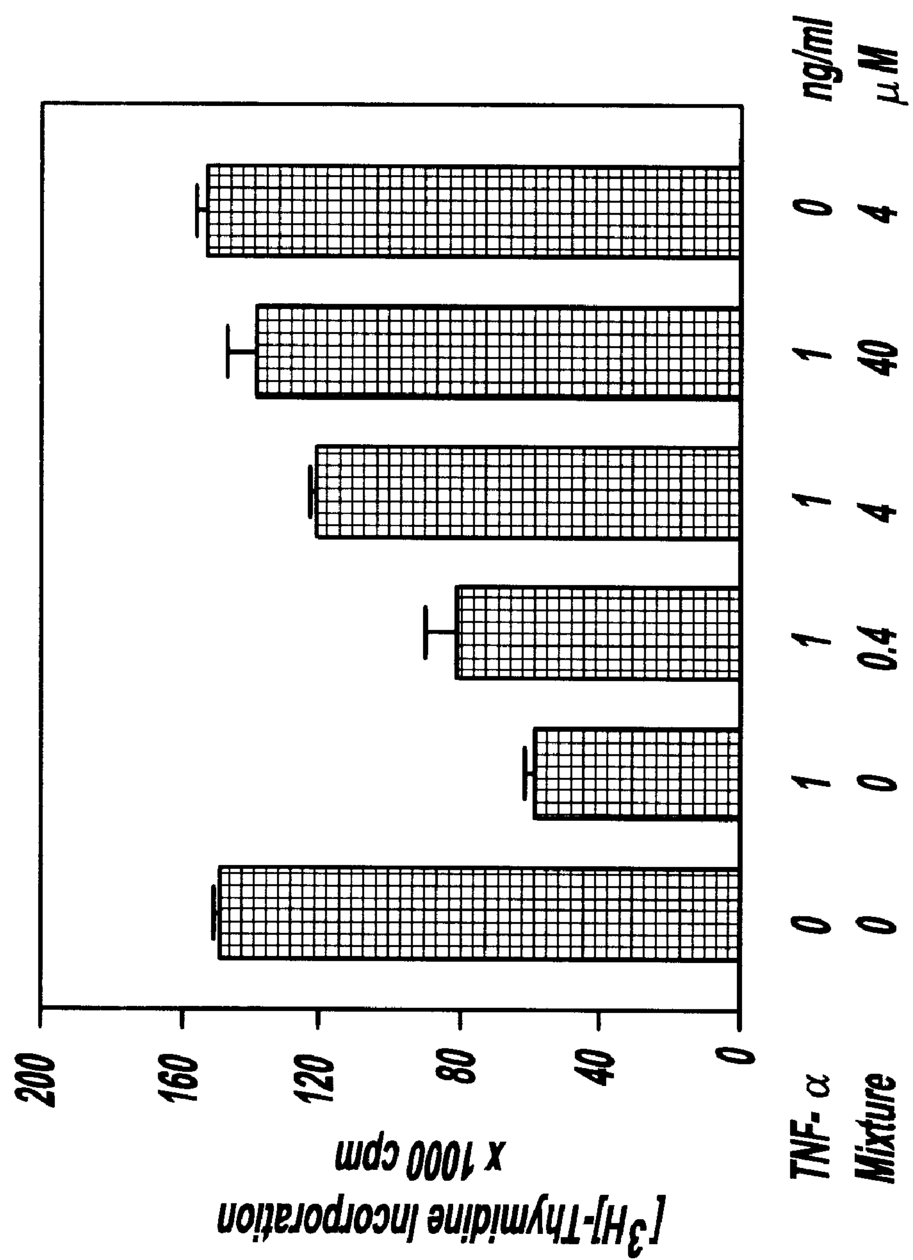
FIG. 5 is a bar graph showing the [$^{3}$H]-thymidine incorporation (×1000 CPM) versus TNF-α (ng/ml) and a mixture.

FIG. 5 is a graph showing the protective effect of peptide mixture on TNF-α-induced inhibition of A549 cell proliferation. A549 cells were incubated for three days with no TNF-α (lane 1), with 1 ng/ml TNF-α and various amounts of peptide mixture (lanes 2–5) and with the mixture only (lane 6). The cells were then labeled with [$^3H$]-thymidine for an additional 4 hours. [$^3H$]-thymidine incorporation was determined from triplicate samples and expressed as mean±SEM of counts per minute of [$^3H$]. The results were similar in three separate experiments performed. The results again showed that TNF-α function is inhibited in a dose-dependent manner, in other words the higher the concentration of the peptide, the greater the inhibition of TNF-α function.

Throughout this application, various publications and patents, are referenced with patents by number and other publications by author and year. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Dinarello C A, Gelfand J A, Wolf S M: Anticytokine strategies in treatment of systemic inflammatory response syndrome. JAMA 269:1829–1834, 1993.

Grewal H P, Mohey el Din A, Gaber L, et al: Amelioration of physiologic and biochemical changes of acute pancreatitis using an anti-TNF-α polyclonal antibody, Amer J Surg 167:214–19, 1994a.

Oppenheim J J, Rossia J L, Gearing A J H: Clinical applications of cytokines; Role in pathogenesis diagnosis and therapy (Oxford University Press, New York, N.Y.) pp. 1–27, 1993.

Physicians' Desk Reference®: pp. 1654–1658, 1994.

Huston et al, 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359–365.

What is claimed is:

1. The method according to claim 1, wherein said administering step further includes singly administering the peptides having the amino acid sequences shown in SEQ ID NO.: 1, 2, 3,4.

2. The method according to claim 1, wherein said administering step further includes combinatorally administering the peptides having amino acids shown in SEQ ID NOS.: 1, 2, 3, 4.

* * * * *

SEQUENCE LISTING

<160> NUMBER OF SEQ ID NOS: 4

<210> SEQ ID NO 1
<211> LENGTH: 7
<212> TYPE: PRT
<213> ORGANISM: Unknown Organism
<220> FEATURE:
<223> OTHER INFORMATION: Description of Unknown Organism: screened from a phage display library

<400> SEQUENCE: 1

Thr Pro Lys His Leu Phe Leu
1 5

<210> SEQ ID NO 2
<211> LENGTH: 7
<212> TYPE: PRT
<213> ORGANISM: Unknown Organism
<220> FEATURE:
<223> OTHER INFORMATION: Description of Unknown Organism: screened from a phage display library

<400> SEQUENCE: 2

Leu Leu Gln Pro Thr Met Asn
1 5

<210> SEQ ID NO 3
<211> LENGTH: 12
<212> TYPE: PRT
<213> ORGANISM: Unknown Organism
<220> FEATURE:
<223> OTHER INFORMATION: Description of Unknown Organism: screened from a phage display library

<400> SEQUENCE: 3

Ser Val Ser Val Gly Met Lys Pro Ser Pro Arg Pro
1 5 10

<210> SEQ ID NO 4
<211> LENGTH: 12
<212> TYPE: PRT
<213> ORGANISM: Unknown Organism
<220> FEATURE:
<223> OTHER INFORMATION: Description of Unknown Organism: screened from a phage display library

<400> SEQUENCE: 4

Phe Ser Pro Leu His Thr Ser Thr Tyr Arg Pro Ser
1 5 10